(12) United States Patent
McBride et al.

(10) Patent No.: US 9,375,240 B2
(45) Date of Patent: Jun. 28, 2016

(54) SPINAL IMPLANT SYSTEM AND METHOD

(71) Applicant: Warsaw Orthropedic, Inc., Warsaw, IN (US)

(72) Inventors: Larry T. McBride, Memphis, TN (US); Keith E. Miller, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 291 days.

(21) Appl. No.: 13/864,816

(22) Filed: Apr. 17, 2013

(65) Prior Publication Data

US 2013/0261679 A1 Oct. 3, 2013

Related U.S. Application Data

(63) Continuation of application No. 13/437,077, filed on Apr. 2, 2012, now Pat. No. 8,439,924.

(51) Int. Cl.
*A61B 17/70* (2006.01)

(52) U.S. Cl.
CPC ........... *A61B 17/7085* (2013.01); *A61B 17/708* (2013.01)

(58) Field of Classification Search
CPC ............. A61B 17/7079; A61B 17/708; A61B 17/7083; A61B 17/7085; A61B 17/7086
USPC .................... 606/246, 90, 99, 104, 105, 86 A
See application file for complete search history.

(56) References Cited

U.S. PATENT DOCUMENTS

| | | | |
|---|---|---|---|
| 3,963,028 A | 6/1976 | Cooley et al. | |
| 5,336,170 A | 8/1994 | Salerno et al. | |
| 5,891,145 A | 4/1999 | Morrison et al. | |
| 7,226,413 B2 | 6/2007 | McKinley | |
| 7,476,240 B2 | 1/2009 | Raymond et al. | |
| 7,491,218 B2 | 2/2009 | Landry et al. | |
| 7,563,264 B2 | 7/2009 | Landry et al. | |
| 7,575,581 B2 | 8/2009 | Lovell | |
| 7,666,189 B2 | 2/2010 | Gerber et al. | |
| 7,794,464 B2 | 9/2010 | Bridwell et al. | |
| 7,802,547 B2 | 9/2010 | Inomoto et al. | |
| 7,842,044 B2 | 11/2010 | Runco et al. | |
| 7,846,093 B2 | 12/2010 | Gorek et al. | |
| 7,854,751 B2 | 12/2010 | Sicvol et al. | |
| 7,887,541 B2 | 2/2011 | Runco et al. | |
| 7,914,558 B2 | 3/2011 | Landry et al. | |
| 7,918,857 B2 | 4/2011 | Dziedzic et al. | |
| 7,918,858 B2 | 4/2011 | Stad et al. | |
| 7,922,746 B2 | 4/2011 | Miller | |
| 7,927,334 B2 | 4/2011 | Miller et al. | |

(Continued)

*Primary Examiner* — Ellen C Hammond
*Assistant Examiner* — Christina Negrellirodrigue

(57) ABSTRACT

A system includes a sleeve including first and second arms each including an outer ramp and an inward projection, each of the arms defining a cavity. First and second extensions are configured for disposal in the cavities. A fastener includes walls defining an implant cavity and a distal portion. The walls each include first and second end surfaces and a locking cavity. The extensions are configured for translation relative to the sleeve between a first orientation such that the extensions engage the respective ramps to fix the projections with a respective locking cavity in a configuration to capture the fastener with the sleeve and a second orientation such that the extensions move out of engagement with the respective ramps so that the projections are movable out of engagement with the locking cavities to release the fastener from the sleeve. Methods of use are disclosed.

16 Claims, 11 Drawing Sheets

(56) References Cited

U.S. PATENT DOCUMENTS

| | | |
|---|---|---|
| 7,985,242 B2 | 7/2011 | Forton et al. |
| 8,012,141 B2 | 9/2011 | Wright et al. |
| 8,096,996 B2 | 1/2012 | Gutierrez et al. |
| 8,211,110 B1 * | 7/2012 | Corin ................. A61B 17/7037 606/104 |
| 8,439,922 B1 * | 5/2013 | Arnold ............... A61B 17/7082 606/104 |
| 2006/0074418 A1 | 4/2006 | Jackson |
| 2006/0079903 A1 | 4/2006 | Wong |
| 2006/0111712 A1 * | 5/2006 | Jackson .......................... 606/61 |
| 2006/0111715 A1 | 5/2006 | Jackson |
| 2006/0111730 A1 | 5/2006 | Hay |
| 2006/0122597 A1 | 6/2006 | Jones et al. |
| 2006/0264962 A1 | 11/2006 | Chin et al. |
| 2006/0293680 A1 | 12/2006 | Jackson |
| 2007/0213714 A1 | 9/2007 | Justis et al. |
| 2007/0244493 A1 | 10/2007 | Bjerken |
| 2007/0270867 A1 | 11/2007 | Miller et al. |
| 2008/0015601 A1 | 1/2008 | Castro et al. |
| 2008/0172062 A1 | 7/2008 | Donahue et al. |
| 2008/0234678 A1 | 9/2008 | Gutierrez et al. |
| 2008/0243190 A1 | 10/2008 | Dziedzic et al. |
| 2009/0105771 A1 | 4/2009 | Lei et al. |
| 2009/0143828 A1 * | 6/2009 | Stad ................... A61B 17/7085 606/86 A |
| 2009/0157125 A1 | 6/2009 | Hoffman et al. |
| 2009/0171391 A1 | 7/2009 | Hutton et al. |
| 2009/0222046 A1 | 9/2009 | Gorek |
| 2009/0228054 A1 | 9/2009 | Hoffman et al. |
| 2009/0228055 A1 | 9/2009 | Jackson |
| 2009/0228056 A1 | 9/2009 | Jackson |
| 2009/0234395 A1 | 9/2009 | Hoffman et al. |
| 2009/0264895 A1 | 10/2009 | Gasperut et al. |
| 2009/0318972 A1 | 12/2009 | Jackson |
| 2010/0030283 A1 | 2/2010 | King et al. |
| 2010/0036443 A1 | 2/2010 | Hutton et al. |
| 2010/0063552 A1 | 3/2010 | Chin et al. |
| 2010/0198268 A1 | 8/2010 | Zhang et al. |
| 2010/0198271 A1 | 8/2010 | Leone |
| 2010/0312279 A1 | 12/2010 | Gephart et al. |
| 2011/0015678 A1 | 1/2011 | Jackson |
| 2011/0022088 A1 | 1/2011 | Forton et al. |
| 2011/0106178 A1 | 5/2011 | Schwab |
| 2011/0202096 A1 | 8/2011 | White et al. |
| 2011/0218581 A1 | 9/2011 | Justis |
| 2011/0264098 A1 | 10/2011 | Cobbs |

* cited by examiner

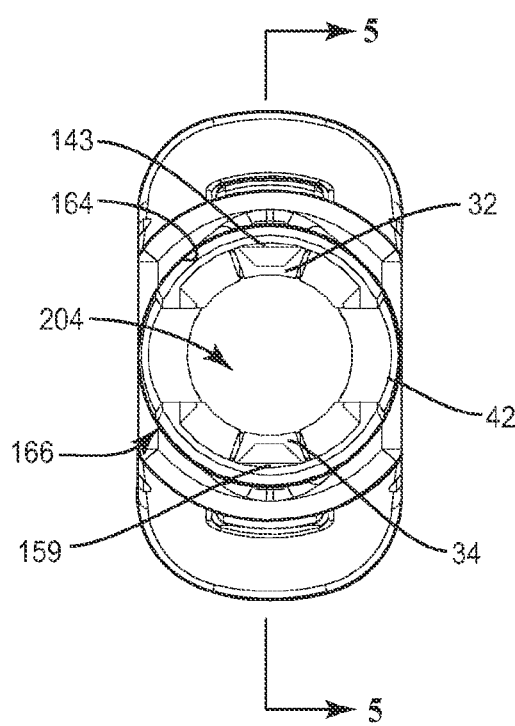
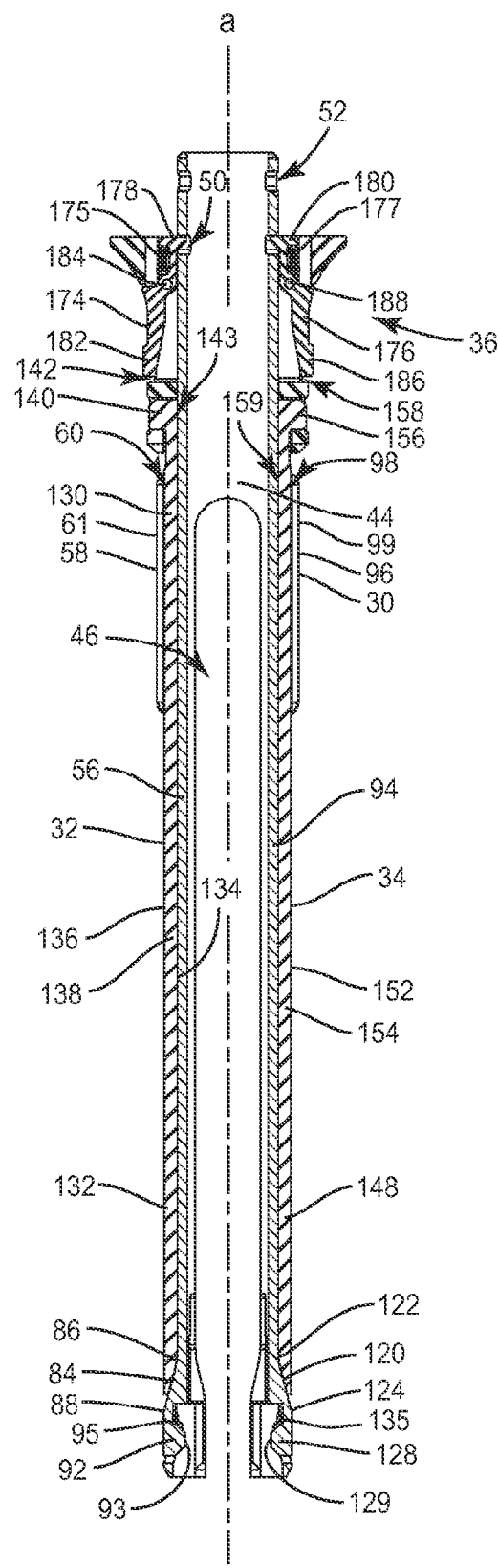
FIG. 4
FIG. 5

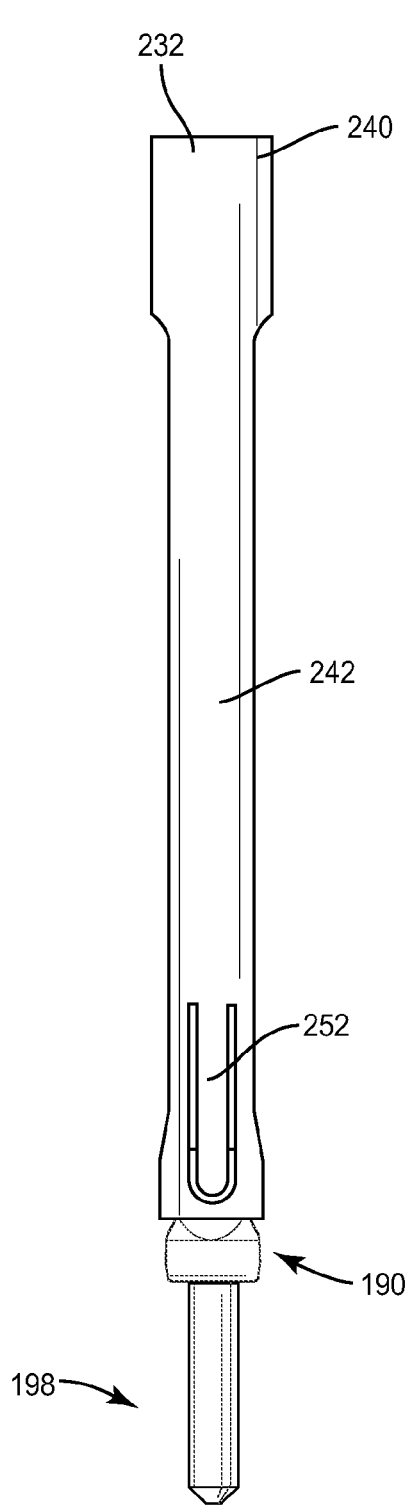
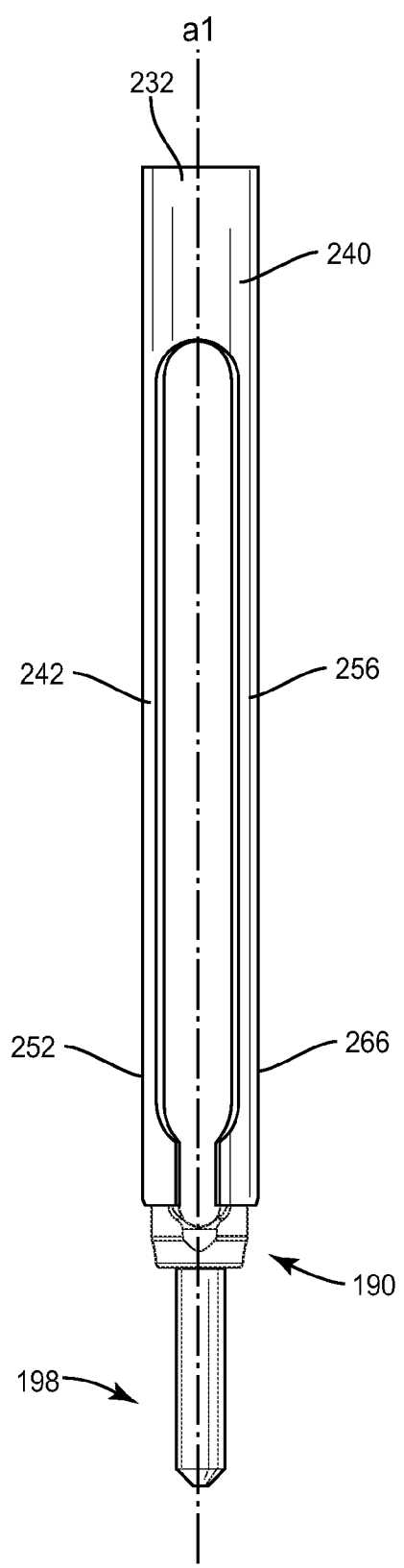
FIG. 17  FIG. 18

SPINAL IMPLANT SYSTEM AND METHOD

CROSS-REFERENCE TO RELATED APPLICATION

This application is a continuation of application Ser. No. 13/437,077, filed on Apr. 2, 2012, now allowed. The contents of this prior application is herein incorporated by reference in its entirety.

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, in accordance with the principles of the present disclosure, a spinal implant system is provided including a sleeve, a first extension, a second extension and a bone fastener. The sleeve defines a longitudinal axis and extends between a first end and a second end. The sleeve includes a first arm, a second arm and an inner surface defining an interior cavity therebetween. Each of the arms include a movable tab having an outer ramp and an inward projection, each of the arms defining a longitudinal cavity. The first extension extends between a first end and a second end, and is configured for movable disposal in the longitudinal cavity of the first arm. The second extension extends between a first end and a second end, and is configured for movable disposal in the longitudinal cavity of the second arm. The bone fastener comprises a proximal portion including two spaced apart walls defining an implant cavity and a distal portion including a tissue engaging portion. The walls each include a first end surface, a second end surface and an outer surface extending therebetween defining a locking cavity. The extensions are configured for axial translation relative to the sleeve between a first orientation and a second orientation. In the first orientation, the second ends of the extensions engage the respective outer ramps to fix the projections with a respective locking cavity in a configuration to capture the bone fastener with the second end of the sleeve. In the second orientation, the second ends of the extensions move out of engagement with the respective outer ramps so that the projections are movable out of engagement the locking cavities to release the bone fastener from the second end of the sleeve.

In one embodiment, the spinal implant system includes a sleeve, a first extension, a second extension and at least one bone fastener. The sleeve defines a longitudinal axis and extends between a proximal end and a distal end. The sleeve includes an inner surface defining a first implant cavity. The sleeve includes a first arm having an arcuate wall that defines a longitudinal channel and includes a first flange having a planar face and a second flange having a planar face adjacent the distal end of the sleeve. The first arm has a tab that is movable in an outward direction and extends between the distal end of the sleeve and an intermediate portion of the sleeve. The tab includes an outer ramp and an inward circular projection. The sleeve includes a second arm having an arcuate wall defining a longitudinal channel and a first flange having a planar face and a second flange having a planar face adjacent the distal end of the sleeve. The second arm has a tab that is movable in an outward direction and extends between the distal end of the sleeve and the intermediate portion of the sleeve. The tab of the second arm includes an outer ramp and an inward circular projection. The first extension extends between a proximal end and a distal end, and is configured for slidable movement within the longitudinal channel of the first arm. The distal end of the first extension is configured for engagement with the outer ramp of the first arm. The second extension extends between a proximal end and a distal end, and is configured for slidable movement within the longitudinal channel of the second arm. The distal end of the second extension is configured for engagement with the ramp of the second arm. The bone fastener(s) comprise(s) a proximal portion including a first wall and a second wall spaced apart from the first wall. The walls define an implant cavity. The bone fastener(s) comprise(s) a distal portion including a tissue engaging portion. The first wall includes a first angled end surface configured to engage the first flange of the first arm, a second angled end surface configured to engage the second flange of the first arm and a first outer surface extending therebetween. The first outer surface includes a first locking cavity. The second wall includes a first angled end surface configured to engage the first flange of the second arm, a second angled end surface configured to engage the second flange of the second arm and a second outer surface extending therebetween. The second outer surface includes a second locking cavity. The extensions are configured for axial translation relative to the sleeve between a first orientation and a second orientation. In the first orientation, the second ends of the extensions engage the respective outer ramps to fix the projections with a respective locking cavity in a configuration to capture the bone fastener with the distal end of the sleeve. In the second orientation, the second ends of the extensions move out of engagement with the respective outer ramps so that the projections are movable out of engagement with the locking cavities to release the bone fastener from the distal end of the sleeve such that the projections are engageable with the edge surfaces so that the sleeve is axially translatable to force the projections outwardly and out of engagement with the locking cavities.

In one embodiment, the spinal implant system includes a sleeve, a first extension, a second extension, an actuator and at least one bone fastener. The sleeve defines a longitudinal axis and extends between a proximal end and a distal end. The sleeve includes an inner surface defining a first implant cavity. The proximal end includes a first lateral opening and a second lateral opening. The sleeve includes a first arm having an arcuate wall that defines a longitudinal channel and includes a first flange having a planar face and a second flange having a planar face adjacent the distal end of the sleeve. The first arm has a tab that is movable in an outward direction and extends between the distal end of the sleeve and an intermediate portion of the sleeve. The tab includes an outer ramp and an inward circular projection having a chamfer surface. The sleeve includes a second arm having an arcuate wall defining a longitudinal channel and a first flange having a planar face and a second flange having a planar face adjacent the second end of the sleeve. The second arm has a tab that is movable in an outward direction and extends between the second end of the sleeve and the intermediate portion of the sleeve. The tab of the second arm includes an outer ramp and an inward circular projection having a chamfer surface. The first extension extends between a proximal end and a distal end, and is configured for slidable movement within the longitudinal channel of the first arm. The distal end of the first extension is configured for engagement with the outer ramp of the first arm. The second extension extends between a proximal end and a distal end, and is configured for slidable movement within the longitudinal channel of the second arm. The distal end of the second extension is configured for engagement with the outer ramp of the second arm. The actuator includes a handle configured to effect axial translation of the extensions relative to the sleeve. The actuator further includes a resiliently biased depressible member rotatable relative to the sleeve and configured for disposal in the first lateral opening in a first orientation and in the second lateral opening in a second orientation. The bone fastener(s) comprise(s) a proximal portion including a first wall and a second wall spaced apart from the first wall. The walls define an implant cavity. The bone fastener(s) comprise(s) a distal portion including a tissue engaging portion. The first wall includes a first angled end surface configured to engage the first flange of the first arm, a second angled end surface configured to engage the second flange of the first arm and a first outer surface extending therebetween. The first outer surface includes an edge surface that defines a first locking cavity. The second wall includes a first angled end surface configured to engage the first flange of the second arm, a second angled end surface configured to engage the second flange of the second arm and a second outer surface extending therebetween. The second outer surface includes an edge that defines a second locking cavity. The handle is manipulable to cause axial translation of the extensions relative to the sleeve between the first orientation and a second orientation. In the first orientation, the second ends of the extensions engage the respective outer ramps to fix the projections with a respective locking cavity in a configuration to capture a bone fastener with the distal end of the sleeve such that the flanges engage the end surfaces to prevent disengagement of the arms from the bone fastener. In the second orientation, the second ends of the extensions move out of engagement with the respective outer ramps so that the projections are movable out of engagement with the locking cavities to release the bone fastener from the distal end of the sleeve such that the projections are engageable with the edge surfaces so that the sleeve is axially translatable to force the projections outwardly and out of engagement with the locking cavities.

BRIEF DESCRIPTION OF THE DRAWINGS

The present disclosure will become more readily apparent from the specific description accompanied by the following drawings, in which:

FIG. 4 is a top view in cross-section of the components shown in FIG. 1;

FIG. 5 is a side view in cross-section of the components shown in FIG. 1;

FIG. 17 is a side view of the components shown in FIG. 16;

FIG. 18 is a side view of the components shown in FIG. 16;

Like reference numerals indicate similar parts throughout the figures.

DETAILED DESCRIPTION

Figure 1:
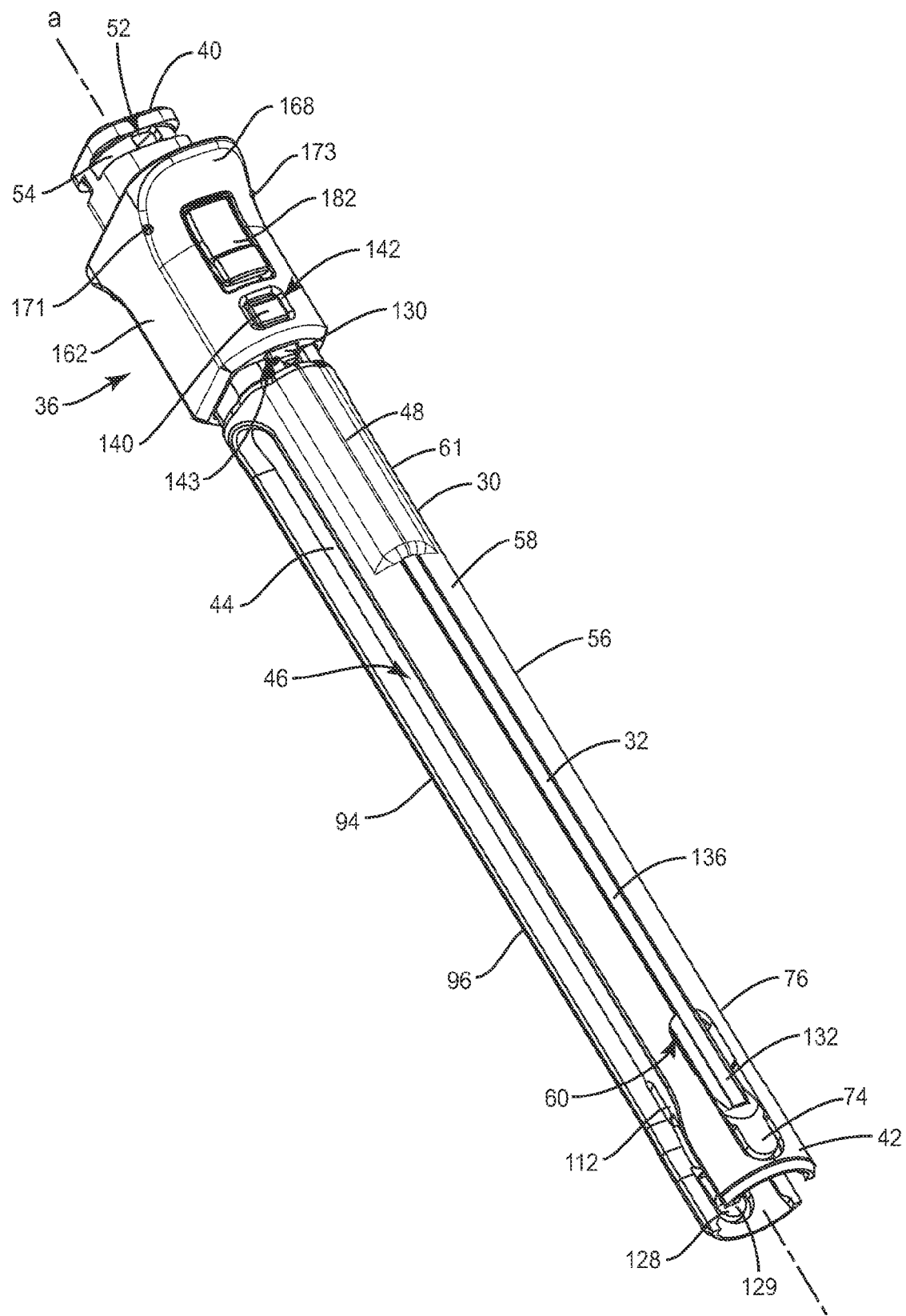
FIG. 1 is a perspective view of components of one particular embodiment of the system in accordance with the principles of the present disclosure.
Figure 2:
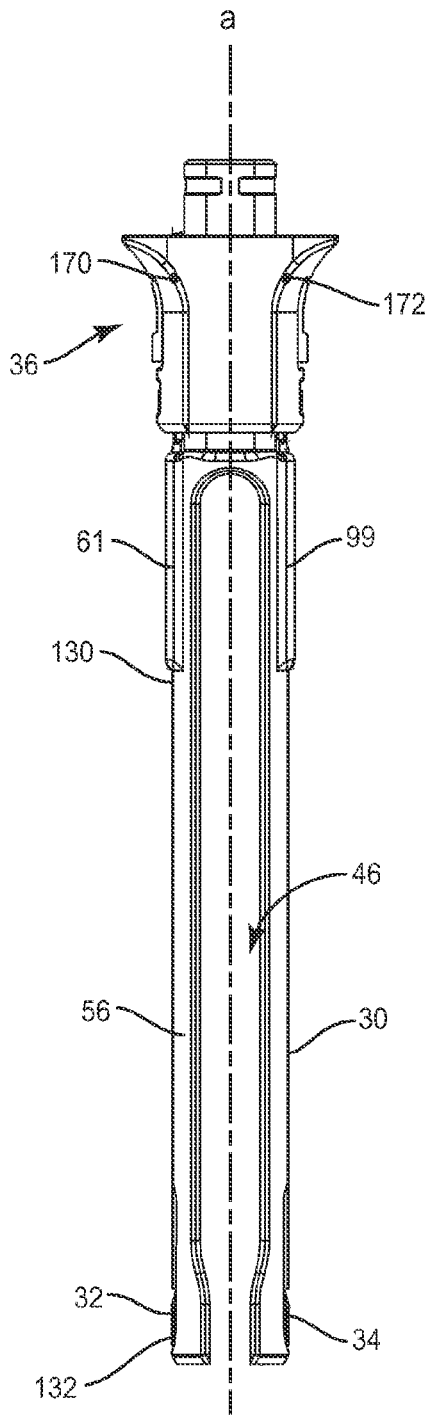
FIG. 2 is a side view of the components shown in FIG. 1.
Figure 3:
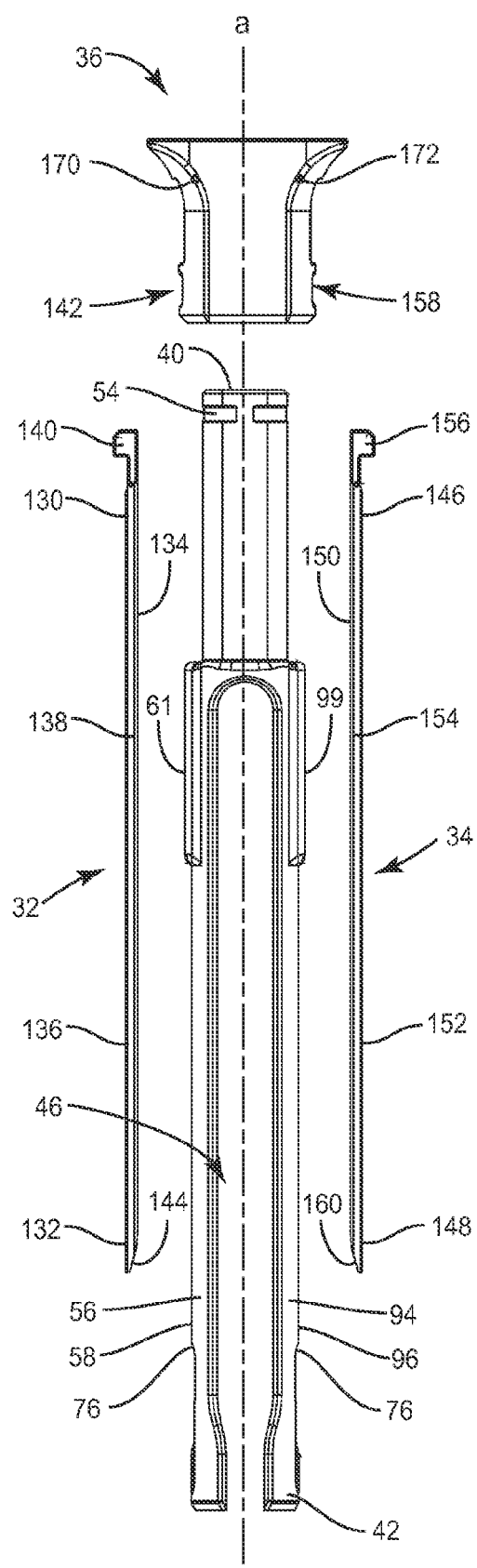
FIG. 3 is a side view of the components shown in FIG. 1, with parts separated.
Figure 6:
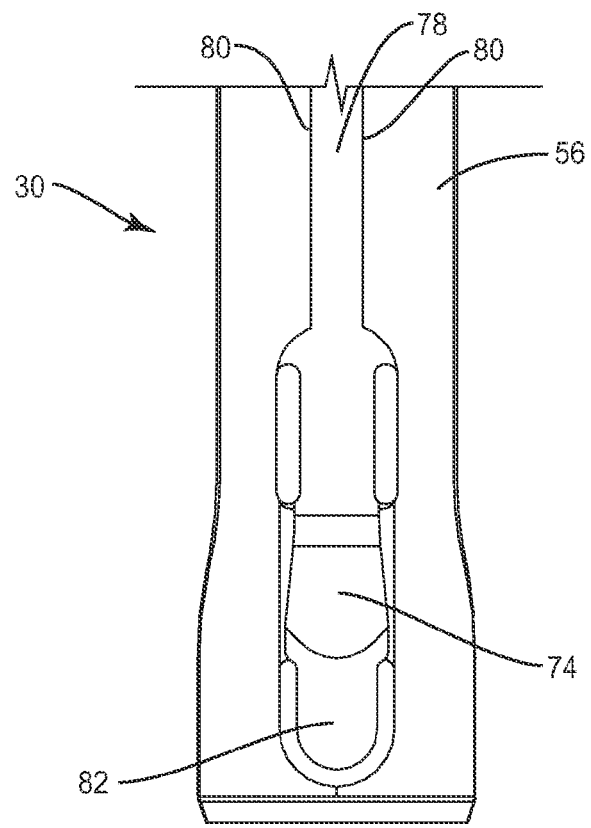
FIG. 6 is a break away side view of the components shown in FIG. 1.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. It is envisioned that the surgical implant system can include a bone fastener having a head with angled surfaces that prevent medial/lateral disengagement of an insertion device, such as, for example, an extender. It is further envisioned that the surgical implant system can include an extender that clicks into engagement with a bone fastener by pushing the extender onto the bone fastener.

It is envisioned that the system may include instruments that are connected or attached to an extender(s) such as, for example, a lateral translation handle or derotaton instruments. It is further envisioned that the system may have an extender with a quick release mechanism to allow the extender to slide in and out of engagement with an implant. It is contemplated that the system can include an extender having features that prevent an implant from rotating. In one embodiment, one or all of the components of the surgical system are disposable, peel-pack, pre-packed sterile devices used with an implant. One or all of the components of the surgical system may be reusable. The surgical system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-15, there is illustrated components of a surgical system, such as, for example, a spinal implant system in accordance with the principles of the present disclosure.

The components of the spinal implant system can be fabricated from biologically acceptable materials suitable for medical applications, including metals, synthetic polymers, ceramics and bone material and/or their composites, depending on the particular application and/or preference of a medical practitioner. For example, the components of the spinal implant system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the spinal implant system may have material composites, including the above materials, to achieve various desired characteristics such as strength, rigidity, elasticity, compliance, biomechanical performance, durability and radiolucency or imaging preference. The components of the spinal implant system, individually or collectively, may also be fabricated from a heterogeneous material such as a combination of two or more of the above-described materials. The components of the spinal implant system may be monolithically formed, integrally connected or include fastening elements and/or instruments, as described herein.

The spinal implant system is employed, for example, with a minimally invasive procedure, including percutaneous techniques, mini-open and open surgical techniques to deliver and introduce an implant, such as, for example, a bone fastener, at a surgical site within a body of a patient, for example, a section of a spine. It is contemplated that the spinal implant system and method may be employed with treatments using minimally invasive and percutaneous techniques.

The spinal implant system includes a sleeve 30, a first extension 32, a second extension 34, an actuator 36 and at least one bone fastener 38. Sleeve 30 defines a longitudinal axis a and extends between a first end, such as, for example, a proximal end 40 and a second end, such as, for example, a distal end 42. Sleeve 30 includes a concavely curved inner surface 44 defining an inner cavity, such as, for example, a first implant cavity 46 and a convexly curved outer surface 48. Implant cavity 46 is configured to facilitate positioning of a spinal construct, such as a vertebral rod, relative to bone fastener 38. It is envisioned that all or only a portion of surface 44, surface 48 and/or implant cavity 46 may be variously configured and dimensioned, such as, for example, planar, concave, convex, polygonal, irregular, uniform, non-uniform, staggered, tapered, consistent or variable, depending on the requirements of a particular application.

Proximal end 40 has a substantially square cross-section, which includes rounded corners (FIG. 3) configured to slidably engage actuator 36. Proximal end 40 of sleeve 30 includes a first lateral opening 50 and a second lateral opening 52. Opening 52 is positioned proximal to opening 50. Each of openings 50, 52 are configured for disposal of at least a portion of actuator 36 to prevent translation of extensions 32, 34 relative to sleeve 30. Openings 50, 52 each extend transverse to longitudinal axis a through surfaces 44, 48 to form a passageway through sleeve 30. It is envisioned that openings 50, 52 may each extend through surface 48 without extending through surface 44 so as to form at least one cavity in sleeve 30. It is further envisioned that openings 50, 52 may extend through surface 48 and/or surface 44 at alternate orientations relative to longitudinal axis a, such as, for example, transverse, perpendicular and/or other angular orientations such as acute or obtuse and/or may be offset or staggered. It is contemplated that sleeve 30 may include one or a plurality of lateral openings. Openings 50, 52 each have a substantially rectangular configuration. It is envisioned that openings 50, 52 may be variously configured and dimensioned, such as, for example, round, oval, oblong, square, rectangular, polygonal, irregular, uniform, non-uniform, offset, staggered, tapered, consistent or variable, depending on the requirements of a particular application.

Proximal end 40 includes at least one transverse groove 54 extending transverse to longitudinal axis a into surface 48 without extending through surface 44. Groove 54 is configured to allow for the attachment of other instruments, such as, for example, drivers and rod reduction instruments with sleeve 30. This feature allows the spinal implant system to be used in other surgical procedures. Groove 54 is aligned with opening 52 such that opening 52 extends through groove 54. It is envisioned that groove 54 may be positioned out of alignment with opening 52, such as, for example, either proximal or distal of opening 52. It is contemplated that sleeve 30 may include one or a plurality of transverse grooves. It is envisioned that groove 54 may have alternate surface configurations to enhance fixation with an instrument such as, for example, rough, arcuate, undulating, mesh, porous, semi-porous, dimpled and/or textured according to the requirements of a particular application. It is further envisioned that groove 54 may extend into surface 48 at alternate orientations relative to longitudinal axis a, such as, for example, transverse, perpendicular and/or other angular orientations such as acute or obtuse and/or may be offset or staggered.

Sleeve 30 includes a first arm 56 having an arcuate wall 58 that defines a longitudinal channel 60. Channel 60 extends parallel to longitudinal axis a and is configured for disposal of extension 32 such that extension 32 can translate axially therein. Channel 60 is defined by a planar bottom surface extending between planar side surfaces that are perpendicular to the planar bottom surface so as to form a channel having a substantially U-shaped cross-section. It is envisioned that channel 60 may have other cross-sectional configurations, including, for example, a cut similar to a rack and pinion, V-shaped, W-shaped, polygonal, or tapered according to the requirements of a particular application. It is further envisioned that wall 58 may be variously configured and dimensioned, such as, for example, planar, concave, convex, polygonal, irregular, uniform, non-uniform, staggered, tapered, consistent or variable, depending on the requirements of a particular application.

Arm 56 includes an enlarged portion 61 disposed adjacent a proximal end thereof. Portion 61 is configured to retain extension 32 in channel 60. Channel 60 extends parallel to longitudinal axis a through portion 61 of to form a passageway through portion 61. It is contemplated that portion 61 may extend the entire length of channel 60. It is further contemplated that channel 60 may extend at various orientations relative to longitudinal axis a, such as, for example, parallel, transverse, perpendicular and/or other angular orientations such as acute or obtuse and/or may be offset or staggered.

Arm 56 includes a first angled flange 62 having a planar face 64 that is parallel with longitudinal axis a. Arm 56 includes a second angled flange 66 having a planar face 68 that is parallel with longitudinal axis a. Flanges 62, 66 are disposed adjacent distal end 42. Face 64 is configured to engage a planar first angled end surface 70 of bone fastener 38 and face 68 is configured to engage a planar second angled end surface 72 of bone fastener 38. Faces 64, 68 engage surfaces 70, 72 to facilitate engagement of sleeve 30 with bone fastener 38 and prevent disengagement of arm 56 from bone fastener 38.

Faces 64, 68 and surfaces 70, 72 each have a surface which is smooth and continuous, uninterrupted by any gaps or protrusions. It is envisioned that faces 64, 68 may extend at various orientations relative to longitudinal axis a, such as, for example, parallel, transverse, perpendicular and/or other angular orientations such as acute or obtuse and/or may be offset or staggered. It is further envisioned that faces 64, 68 and/or surfaces 70, 72 may be variously configured and dimensioned, such as, for example, planar, concave, convex, polygonal, irregular, uniform, non-uniform, staggered, tapered, consistent or variable, depending on the requirements of a particular application. It is contemplated that all or a portion of faces 64, 68 and/or surfaces 70, 72 may have alternate surface fixation configurations, such as, for example, rough, undulating, porous, semi-porous, dimpled, polished and/or textured according to the requirements of a particular application. It is further contemplated that sleeve 30 may engage bone fastener 38 and prevent sleeve 30 from rotating relative to bone fastener 38 about longitudinal axis a in alternate fixation configurations, such as, for example, friction fit, pressure fit, locking protrusion/recess, locking keyway and/or adhesive.

Arm 56 includes a movable tab 74 extending between distal end 42 and an intermediate portion 76 of sleeve 30. Tab 74 includes a proximal portion 78 defined by a pair of parallel planar sidewalls 80 and a distal portion 82, which is non-uniform. It is envisioned that all or a portion of tab 74 may be variously configured and dimensioned, such as, for example, planar, concave, convex, polygonal, irregular, uniform, non-uniform, staggered, tapered, consistent or variable, depending on the requirements of a particular application. It is further envisioned that all or a portion of tab 74 may be radially flexible to facilitate connection to and removal from bone fastener 38. It is contemplated that tab 74 may be resilient to maintain the connection between tab 74 and bone fastener 38.

Inner surface 44 includes a curved first transverse wall 45 and a curved second transverse wall 47. Walls 45, 47 each have a curvature, which is continuous with surface 44. Wall 45 defines a first ridge 49 and wall 47 defines a second ridge 51. Ridges 49, 51 each define a planar face. Ridges 49, 51 are configured to engage at least a portion of bone fastener 38 to prevent movement of bone fastener 38 relative to sleeve 30 in an axial direction.

An inner surface of portion 78 defines a ledge 79 that is coplanar with ridge 49 and has a curvature that is continuous with wall 45. Ridge 49 and ledge 79 define a U-shaped wall configured to engage at least a portion of bone fastener 38 to prevent movement of bone fastener 38 relative to arm 56 in an axial direction.

Figure 7:
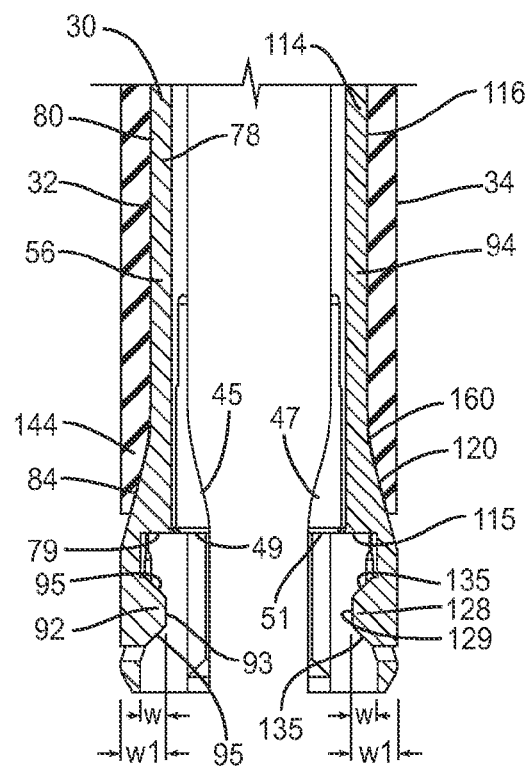
FIG. 7 is a break away side view in cross-section of the components shown in FIG. 6.
Figure 8:
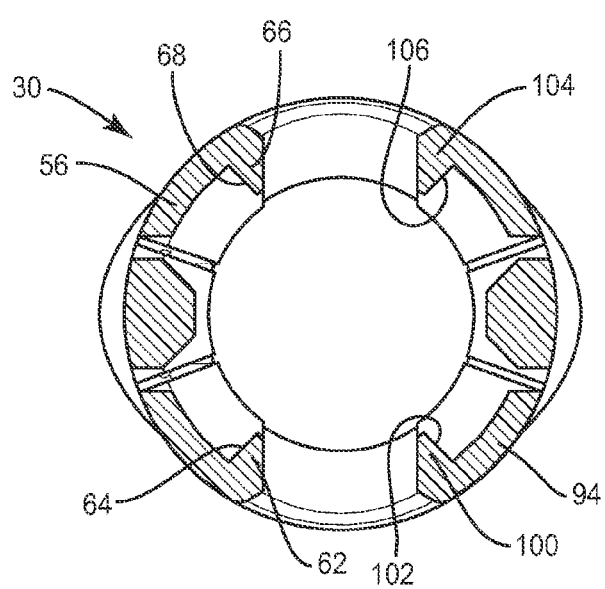
FIG. 8 is a bottom view in cross-section of the components shown in FIG. 6.
Figure 10:
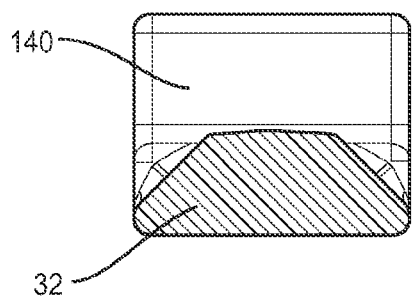
FIG. 10 is a side view in cross-section of the component shown in FIG. 9.
Figure 9:
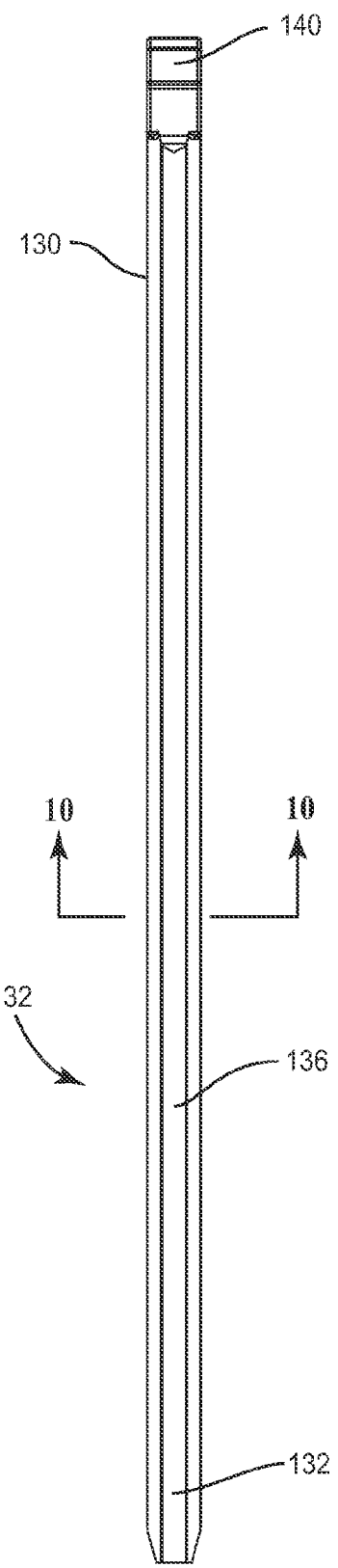
FIG. 9 is a side view of a component of one particular embodiment of the system in accordance with the principles of the present disclosure.
Figure 11:
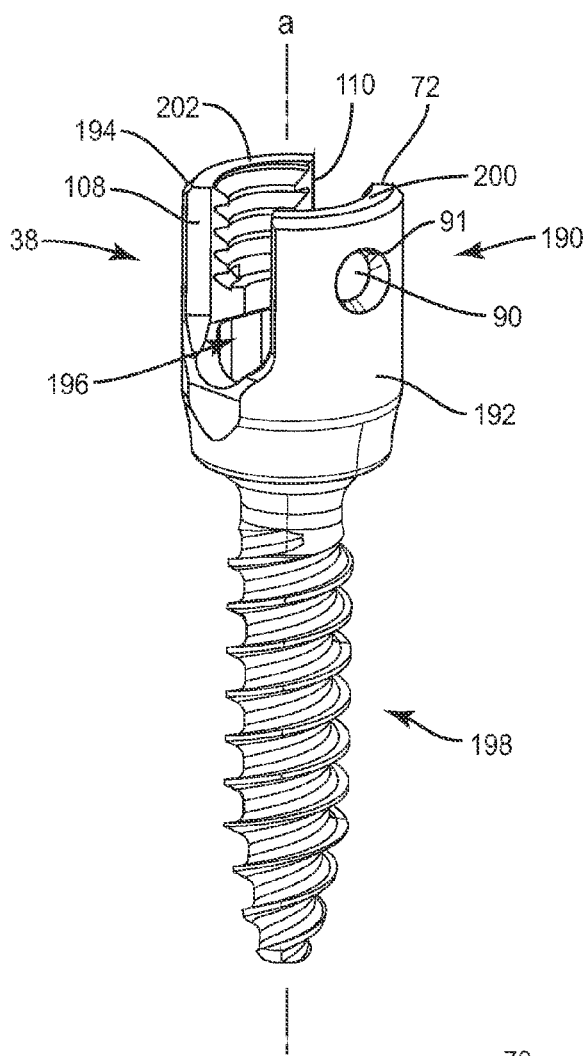
FIG. 11 is a perspective view of a component of one particular embodiment of the system in accordance with the principles of the present disclosure.
Figure 12:
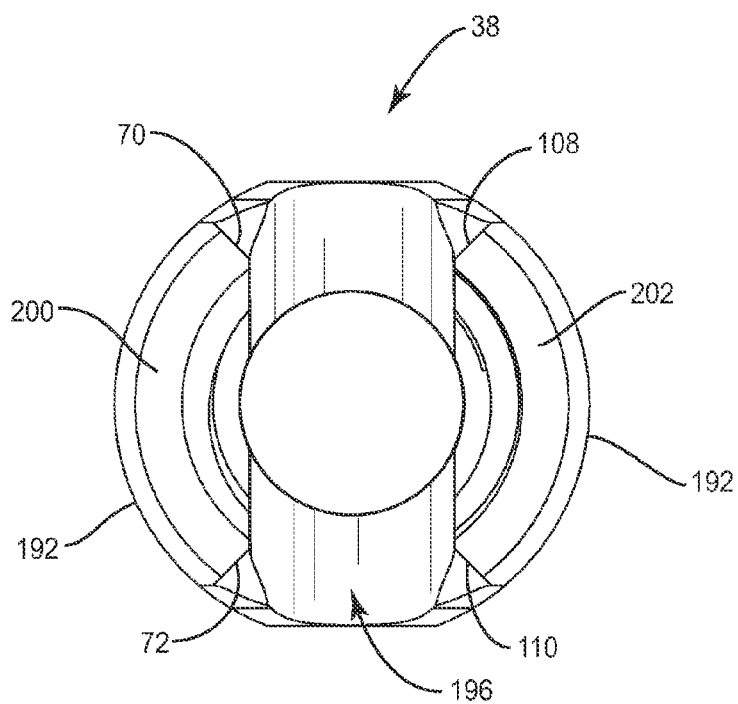
FIG. 12 is a top view of the component shown in FIG. 11.

Tab 74 includes an outer ramp 84 extending from outer surface 48 along longitudinal axis a. Ramp 84 is tapered between a first end 86 having a width w and a second end 88 having a width w1. Width w1 is greater than width w (FIG. 7). Ramp 84 is planar between end 86 and end 88 and is configured to engage extension 32 so that an inward circular projection 92 of tab 74 is movable out of engagement with a locking cavity 90 in bone fastener 38 to release bone fastener 38 from end 42, as will be discussed.

Locking cavity 90 is substantially circular and defined by an edge surface 91 and a planar wall surface of bone fastener 38. It is envisioned that all or a portion of the surface of locking cavity 90 may be, for example, planar, concave, convex, polygonal, irregular, uniform, non-uniform, staggered, tapered, consistent or variable, depending on the requirements of a particular application. It is further envisioned that locking cavity 90 may be variously configured, such as, for example, round, oval, oblong, square, rectangular, polygonal, irregular, uniform, non-uniform, offset, staggered, tapered, consistent or variable, depending on the requirements of a particular application. Edge surface 91 has a radial band configuration disposed about locking cavity 90 and extends a wall thickness to the planar wall surface of bone fastener 38. Surface 91 is engageable with projection 92 to move projection 92 out of engagement with locking cavity 90 to release bone fastener 38 from end 42, as will be discussed.

Figure 14:
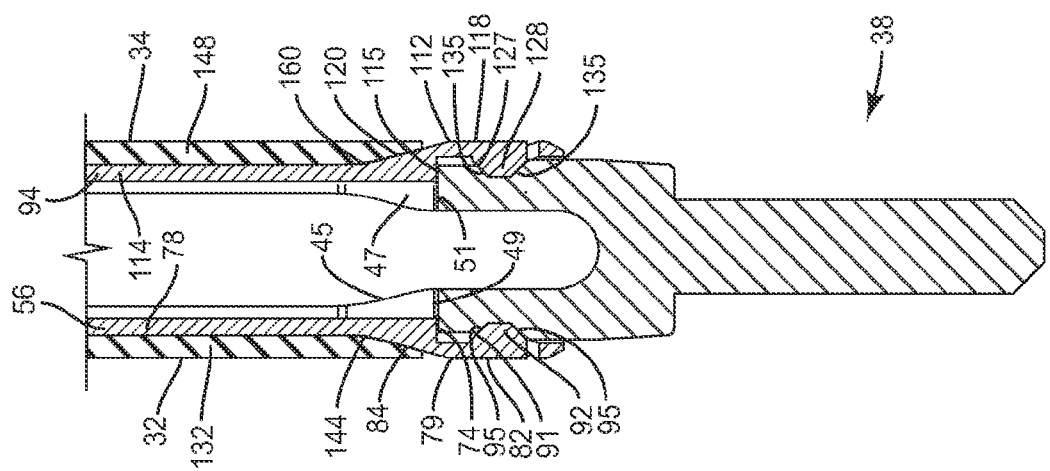
FIG. 14 is a break away side view in cross-section of the system shown in FIG. 13.

Projection 92 extends transverse to longitudinal axis a from surface 44. Projection 92 includes a planar face 93 and is configured for fixation with locking cavity 90 to capture bone fastener 38 with end 42. Projection 92 includes a circumferential chamfer 95 adjacent face 93 such that projection 92 is tapered. Chamfer 95 engages surface 91 as extensions 32, 34 are advanced distally to securely retain projection 92 within locking cavity 90 when projection 92 is aligned with locking cavity 90 (FIG. 14).

Tab 74 is configured to move through a range of motion sufficient to allow engagement and disengagement of bone fastener 38. Chamfer 95 engages surface 91 as arm 56 translates axially relative to bone fastener 38 to force projection 92 outwardly and out of engagement with locking cavity 90 to release bone fastener 38 from end 42. It is envisioned that projection 92 may extend from inner surface 44 at various orientations relative to longitudinal axis a, such as, for example, parallel, transverse, perpendicular and/or other angular orientations such as acute or obtuse and/or may be offset or staggered. It is further envisioned that projection 92 may be variously configured and dimensioned, such as, for example, round, oval, oblong, square, rectangular, polygonal, irregular, uniform, non-uniform, offset, staggered, tapered, consistent or variable, depending on the requirements of a particular application. It is contemplated that bone fastener 38 may be captured with distal end 42 in alternate fixation configurations, such as, for example, friction fit, pressure fit, locking protrusion/recess, locking keyway and/or adhesive.

Sleeve 30 includes a second arm 94, similar to arm 56, including an arcuate wall 96 that defines a longitudinal channel 98. Channel 98 extends parallel to longitudinal axis a and is configured for disposal of extension 34 such that extension 34 can translate axially therein. Channel 98 is defined by a planar bottom surface extending between planar side surfaces that are perpendicular to the planar bottom surface so as to form a channel having a substantially U-shaped cross-section. Arm 94 includes an enlarged portion 99 disposed adjacent a proximal end thereof. Portion 99 is configured to retain extension 34 in channel 98. Channel 98 extends parallel to longitudinal axis a through portion 99 of to form a passageway through portion 99.

Arm 94 includes a first angled flange 100 having a planar face 102 that is parallel with longitudinal axis a. Arm 94 includes a second angled flange 104 having a planar face 106 that is parallel with longitudinal axis a. Flanges 62, 66 are disposed adjacent distal end 42. Face 102 is configured to engage a planar first angled end surface 108 of bone fastener 38 and face 106 is configured to engage a planar second angled end surface 110 of bone fastener 38. Faces 102, 106 engage surfaces 108, 110 to facilitate engagement of sleeve 30 with bone fastener 38 and prevent disengagement of arm 94 from bone fastener 38. Planar faces 102, 104 and surfaces 108, 110 each have a surface that is smooth and continuous, uninterrupted by any gaps or protrusions.

Arm 94 includes a movable tab 112 extending between distal end 42 and intermediate portion 76. Tab 112 includes a proximal portion 114 defined by a pair of parallel planar sidewalls 116 and a distal portion 118, which is non-uniform. An inner surface of portion 114 defines a ledge 115 that is coplanar with ridge 51 and has a curvature that is continuous with wall 47. Ridge 51 and ledge 115 define a U-shaped wall configured to engage at least a portion of bone fastener 38 to prevent movement of bone fastener 38 relative to arm 94 in an axial direction.

Tab 112 includes an outer ramp 120 extending from surface 48 along longitudinal axis a. Ramp 120 is tapered between a first end 122 having a width w and a second end 124 having a width w1. Width w1 is greater than width w. Ramp 120 is planar between end 122 and end 124 and is configured to engage extension 34 so that an inward circular projection 128 of tab 112 is movable out of engagement with a locking cavity 126 in bone fastener 38 to release bone fastener 38 from end 42, similar to cavity 90 and projection 92.

Projection 128 extends transverse to longitudinal axis a from surface 44. Projection 128 includes a planar face 129 and is configured for fixation with locking cavity 126 to capture bone fastener 38 with end 42. Projection 128 includes a circumferential chamfer 135 adjacent face 129 such that projection 128 is tapered. Chamfer 135 engages surface 127 to securely retain projection 128 within locking cavity 126 when projection 128 is aligned with locking cavity 126. Chamfer 135 also engages surface 127 as arm 94 translates axially relative to bone fastener 38 to move projection 128 in and out of engagement with locking cavity 126, as will be discussed.

Extension 32 extends between a first end, such as, for example, a proximal end 130 and a second end, such as, for example, a distal end 132. Extension 32 is configured for slidable movement within longitudinal channel 60. Extension 32 includes a planar first surface 134 configured to slidably engage the planar bottom surface of longitudinal channel 60 and an arcuate second surface 136, opposite surface 134. Extension 32 includes planar side surfaces 138 extending between surfaces 134, 136. Surfaces 138 engage the planar side surfaces of longitudinal channel 60 when extension 32 is disposed within longitudinal channel 60 to maintain extension 32 within longitudinal channel 60 during axial translation of first extension 32 relative to sleeve 30 along longitudinal axis a. Extension 32 has a height between surfaces 134, 136 which is approximately equal to a depth of longitudinal channel 60. Surface 136 has a curvature that is similar to that of arcuate wall 58 such that first surface 136 and arcuate wall 58 form a convexly curved wall having a continuous curvature when first extension 32 is disposed within longitudinal channel 60.

End 130 includes a flange portion 140 configured for disposal in a first aperture 142 of actuator 36 to fix extension 32 with actuator 36. Aperture 142 is substantially rectangular. Portion 140 is securely retained within aperture 142. Aperture 142 is in communication with a longitudinal channel 143 extending along longitudinal axis a. Channel 143 extends through a portion of actuator 36 and is configured for disposal of end 130 when portion 140 is disposed in aperture 142. Surface 134 includes a tapered portion 144 at end 132 configured for engagement with ramp 84. Portion 144 extends through surface 134 at an angle which is approximately equivalent to the angle in which ramp 84 extends from surface 48 such that surface 48 is aligned with surface 136 at end 82 when portion 144 engages ramp 84. In one embodiment, end 130 has an opening extending through surfaces 134, 136; a pin may extend through the opening in end 130 and into a portion of actuator 36 to fix extension 32 with actuator 36. It is envisioned that extension 32 may be fixed with actuator 36 in alternate fixation configurations, such as, for example, friction fit, pressure fit, locking protrusion/recess, locking keyway and/or adhesive.

Extension 34 extends between a first end, such as, for example, a proximal end 146 and a second end, such as, for example, a distal end 148. Extension 34 is configured for slidable movement within longitudinal channel 98. Extension 34 includes a planar first surface 150 configured to slidably engage the planar bottom surface of longitudinal channel 98 and an arcuate second surface 152, opposite surface 150. Extension 34 includes planar side surfaces 154 extending between surfaces 150, 152.

End 146 includes a flange portion 156 configured for disposal in a second aperture 158 in actuator 36 to fix extension 34 with actuator 36. Aperture 158 is substantially rectangular. Portion 156 is substantially rectangular such that portion 156 is securely retained within aperture 158. Aperture 158 is in communication with a longitudinal channel 159 extending along longitudinal axis a. Aperture 158 extends through a portion of actuator 36 and is configured for disposal of end 146 when portion 156 is disposed in aperture 158. Surface 154 includes a tapered portion 160 at end 148 configured for engagement with ramp 120. In one embodiment, end 146 has an opening extending through surfaces 150, 152; a pin may extend through the opening in end 146 and into a portion of actuator 36 to fix extension 34 with actuator 36.

Actuator 36 includes a handle 162 configured to effect axial translation of extensions 32, 34 relative to sleeve 30. Handle 162 includes an inner surface 164 defining a substantially square passageway 166 having rounded corners (FIG. 4) configured for disposal of end 40 such that end 40 can translate axially within passageway 166 along longitudinal axis a. Handle 162 includes an outer surface 168 disposed opposite to surface 162. Apertures 142, 158 each extend through surface 164 and surface 168. Longitudinal channels 143, 159 extend through surface 164 without extending through surface 168.

Actuator 36 includes a first cylindrical channel 170 extending transverse to longitudinal axis a through surface 164. An outer surface 168 and longitudinal channel 143 are configured for disposal of a cylindrical pin 171. A second cylindrical channel 172 extends transverse to longitudinal axis a through surface 164. Surface 168 and longitudinal channel 159 are configured for disposal of a cylindrical pin 173. It is envisioned that cylindrical channels 170, 172 may be disposed in an orientation relative to longitudinal axis a, for example, perpendicular and/or selected angular orientations such as acute or obtuse, perpendicular and/or parallel.

Actuator 36 includes a first resiliently biased depressible member 174 and a second resiliently biased depressible member 176. Members 174, 176 are rotatable relative to sleeve 30. Member 174 includes a tip 178 configured for disposal in opening 50 in a first orientation when extensions 32, 34 are in a first orientation and in lateral opening 52 when extensions 32, 34 are in a second orientation. Member 176 includes a tip 180 configured for disposal in opening 50 when extensions 32, 34 are in the first orientation and in opening 52 when extensions 32, 34 are in the second orientation.

Member 174 includes a button 182 and a cylindrical opening 184 extending transverse to longitudinal axis a through member 174. Opening 184 is configured for disposal of pin 171 such that member 174 is rotatable relative to sleeve 30 about pin 171. Member 174 includes a first biasing member, such as, for example, a spring 175 disposed between sleeve 30 and tip 178 to bias tip 178 inwardly for disposal in opening 50 when extensions 32, 34 are in the first orientation or opening 52 when extensions 32, 34 are in the second orientation. Member 176 includes a button 186 and a cylindrical opening 188 extending transverse to longitudinal axis a through member 176. Opening 188 is configured for disposal of pin 173 such that member 176 is rotatable relative to sleeve 30 about pin 173. Member 176 includes a second biasing member, such as, for example, a spring 177 disposed between sleeve 30 and tip 180 to bias tip 180 inwardly for disposal in opening 50 when extensions 32, 34 are in the first orientation or opening 52 when extensions 32, 34 are in the second orientation.

Bone fastener 38 includes a proximal portion, such as, for example, a receiver 190 having a first wall 192 and a second wall 194 spaced apart from first wall 192. Walls 192, 194 extend parallel to longitudinal axis a. Walls 192, 194 define an implant cavity 196. Bone fastener 38 includes a distal tissue engaging portion, such as, for example, a shaft 198. It is envisioned that the tissue engaging portion of bone fastener 38 may be configured to penetrate tissue. It is further envisioned that the tissue engaging portion of bone fastener 38 may comprise a screw, a hook, a clamp, or other mechanism configured to engage bone or other tissue.

Wall 192 includes first and second end surfaces that define surfaces 70, 72, which each extend parallel to longitudinal axis a. Wall 192 includes a planar face 200 extending between surfaces 70, 72. Face 200 is configured to engage the U-shaped wall defined by ridge 49 and ledge 79 to prevent movement of bone fastener 38 relative to arm 56 in an axial direction (FIG. 14). Locking cavity 90 extends transverse to longitudinal axis a through the first outer surface of bone fastener 38. Wall 194 includes first and second end surfaces that define surfaces 108, 110, which each extend parallel to longitudinal axis a. Wall 194 includes a planar face 202 extending between surfaces 108, 110. Face 202 is configured to engage the U-shaped wall defined by ridge 51 and ledge 115 to prevent movement of bone fastener 38 relative to arm 94 in an axial direction (FIG. 14). Locking cavity 126 extends transverse to longitudinal axis a through the second outer surface of bone fastener 38. It is contemplated that walls 192, 194, surfaces 70, 72 and/or surfaces 108, 110 may be disposed at alternate orientations, relative to longitudinal axis, such as, for example, transverse, perpendicular and/or other angular orientations such as acute or obtuse, co-axial and/or may be offset or staggered.

At least a portion of an inner surface of receiver 190 is threaded and engageable with a coupling member, such as, for example, a setscrew. It is envisioned that the inner surface of receiver 190 can include a thread form located adjacent wall 192 and a thread form located adjacent wall 194 each configured for engagement with a setscrew. It is envisioned that the inner surface of receiver 190 may be disposed with the setscrew in alternate fixation configurations, such as, for example, friction fit, pressure fit, locking protrusion/recess, locking keyway and/or adhesive. It is contemplated that all or only a portion of the inner surface of receiver 190 may have alternate surface configurations to enhance fixation with the setscrew such as, for example, rough, arcuate, undulating, mesh, porous, semi-porous, dimpled and/or textured according to the requirements of a particular application.

Shaft 198 is threaded along a length thereof and has a cylindrical cross section configuration. Shaft 198 includes an outer surface having an external thread form. It is contemplated that the thread form may include a single thread turn or a plurality of discrete threads. It is further contemplated that other engaging structures may be located on shaft 198, such as, for example, a nail configuration, barbs, expanding elements, raised elements and/or spikes to facilitate engagement of shaft 198 with tissue, such as, for example, vertebrae and/or iliac bone. It is envisioned that all or only a portion of shaft 198 may have alternate cross section configurations, such as, for example, oval, oblong, triangular, square, polygonal, irregular, uniform, non-uniform, offset, staggered, undulating, arcuate, variable and/or tapered. It is contemplated that the outer surface of shaft 198 may include one or a plurality of openings. It is further contemplated that all or only a portion of the outer surface of shaft 198 may have alternate surface configurations to enhance fixation with tissue such as, for example, rough, arcuate, undulating, mesh, porous, semi-porous, dimpled and/or textured according to the requirements of a particular application. It is envisioned that all or only a portion of shaft 198 may be disposed at various orientations, relative to longitudinal axis a, such as, for example, transverse, perpendicular and/or other angular orientations such as acute or obtuse and/or may be offset or staggered. It is further envisioned that all or only a portion of shaft 198 may be cannulated.

In operation, extension 32 is disposed in longitudinal channel 60. Flange portion 140 is disposed in aperture 142. Extension 34 is disposed in longitudinal channel 98 and flange portion 156 is disposed in aperture 158. Actuator 36 is mounted on end 40. End 42 is positioned adjacent bone fastener 38 such that faces 64, 68 are aligned with surfaces 70, 72. Faces 102, 106 are aligned with surfaces 108, 110.

Distal end 42 may be advanced distally along longitudinal axis a over bone fastener 38 such that faces 64, 68 engage surfaces 70, 72 and faces 102, 106 engage surfaces 108, 110 to retain sleeve 30 with bone fastener 38 in a first orientation, prevent rotation of sleeve 30 relative to bone fastener 38 about longitudinal axis a and prevent sleeve 30 from moving from bone fastener 38 perpendicular to longitudinal axis a. The U-shaped wall defined by ridge 49 and ledge 79 engages face 200 and the U-shaped wall defined by ridge 51 and ledge 115 engages face 202. Projections 92, 128 are aligned with locking cavities 90, 126 and chamfers 95, 135 slide along surfaces 91, 127 such that projections 92, 128 move into locking cavities 90, 126 to retain sleeve 30 with bone fastener 38.

Handle 162 is manipulable to cause axial translation of extensions 32, 34 relative to sleeve 30. To provisionally capture bone fastener 38, button 182 is pressed to overcome the force of spring 175 and button 186 is pressed simultaneously to overcome the force of spring 177 to permit actuator 36 to advance distally along longitudinal axis a. As actuator 36 is advanced distally, portion 144 is advanced from end 86 to end 88 and portion 160 is advanced from end 122 to end 124 such that distal ends 132, 148 engage ramps 84, 120 such that projections 92, 128 are not dis-engageable, removable and/or movable out from locking cavities 90, 126 (FIG. 14). In the first orientation, projections 92, 128 are fixed within locking cavities 90, 126. Buttons 182, 186 may be released such that springs 175, 177 each apply a force to insert tips 178, 180 into lateral openings 50.

To move extensions 32, 34 to the second orientation, button 182 is pressed to overcome the force of spring 175 and button 186 is pressed simultaneously to overcome the force of spring 177 to withdraw tips 178, 180 from lateral openings 50 so as to permit actuator 36 to advance proximally along longitudinal axis a and allow tabs 74, 112 to move out of engagement with locking cavities 90, 126 to release bone fastener 38 from sleeve 30. Actuator 36 may be advanced proximally along longitudinal axis a until tips 178, 180 are aligned with openings 52. As actuator 36 is advanced proximally, portion 144 is advanced from end 88 to end 86 and portion 160 is advanced from end 124 to end 122 such that ends 132, 148 disengage ramps 84, 120. This configuration allows projections 92, 128 to disengage from locking cavities 90, 126.

Figure 13:
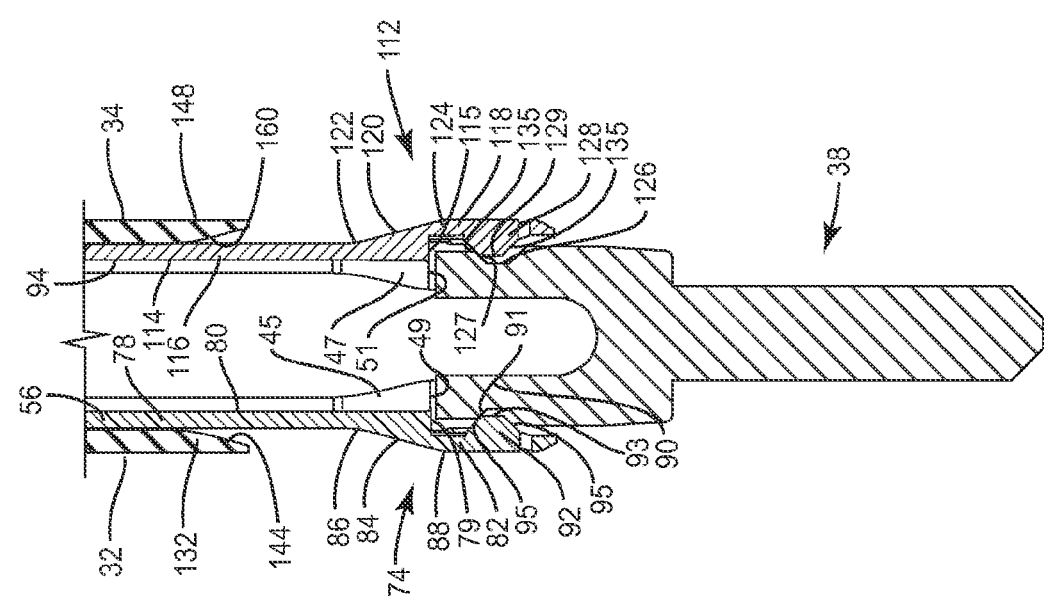
FIG. 13 is a break away side view in cross-section of one particular embodiment of the system in accordance with the principles of the present disclosure.

As sleeve 30 is advanced proximally, chamfers 95, 135 engage and slide along surfaces 91, 127 forcing projections 92, 128 out of engagement with locking cavities 90, 126 (FIG. 13). Actuator 36 may be advanced proximally along longitudinal axis a until tips 178, 180 are aligned with openings 52. Buttons 182, 186 may be released such that springs 175, 177 each apply a force to insert tips 178, 180 into openings 52.

Figure 15:
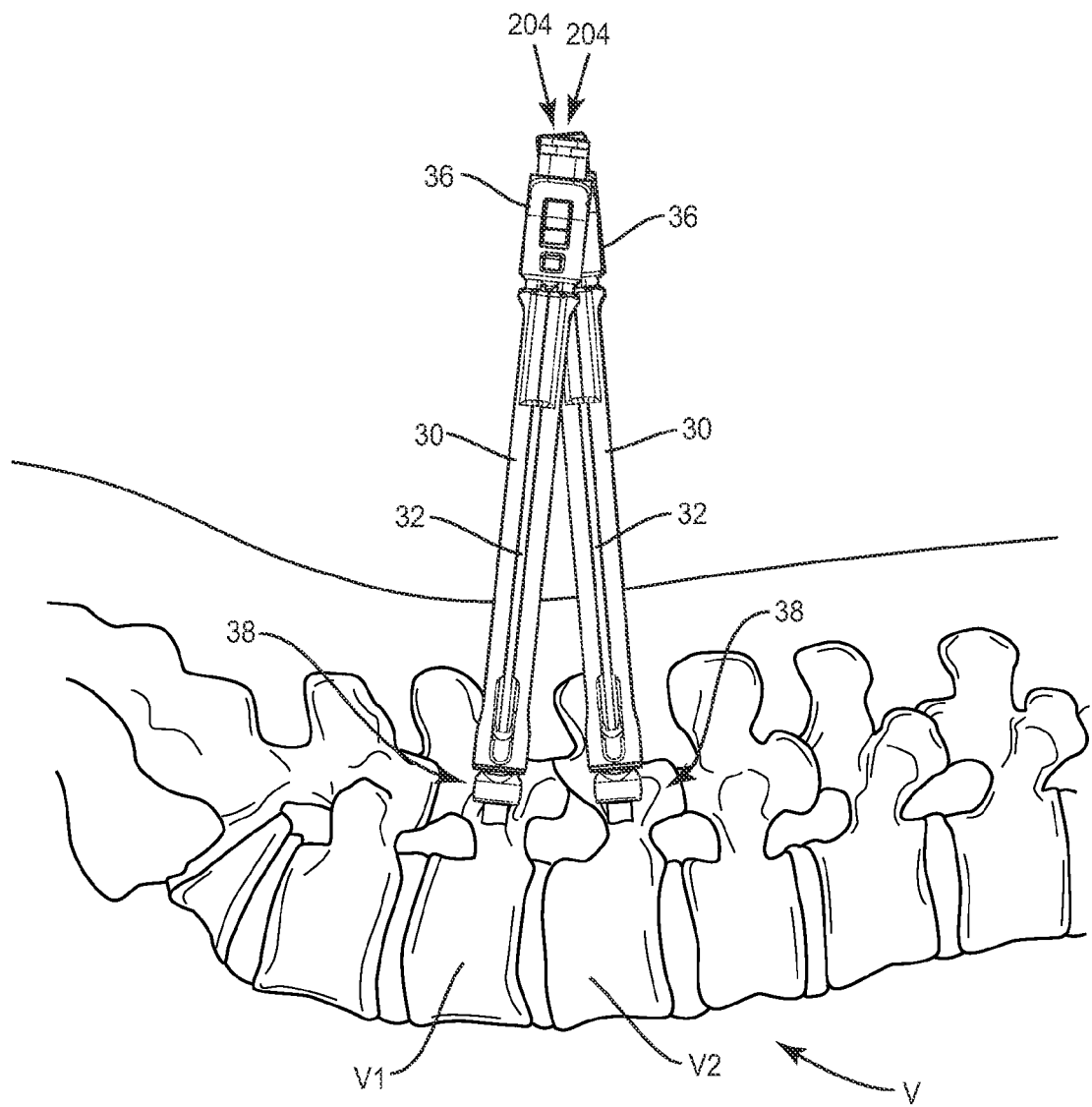
FIG. 15 is a plan view of the system shown in FIG. 13 attached with vertebrae of a patient.
Figure 16:
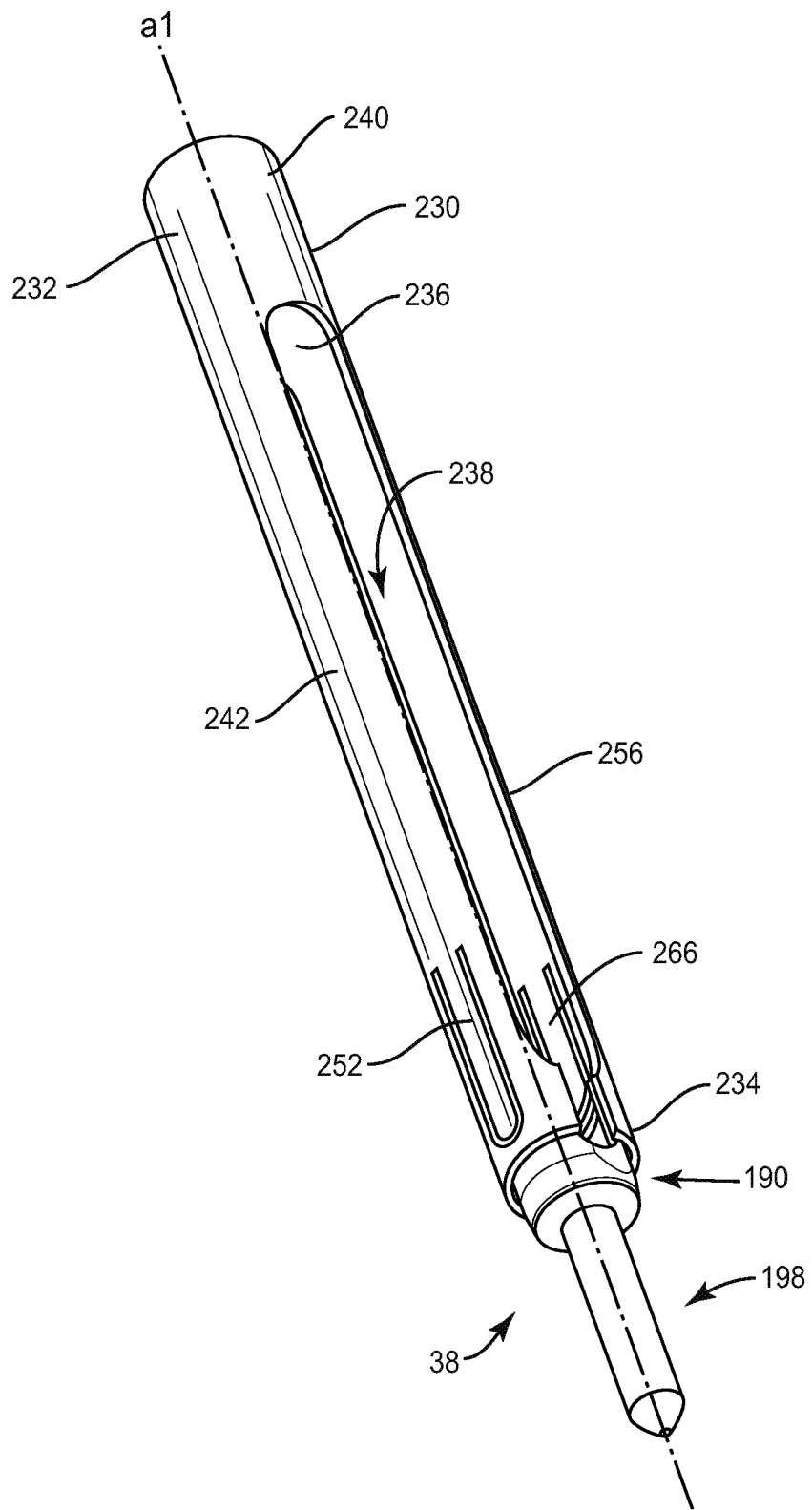
FIG. 16 is perspective view of components of one particular embodiment of a system in accordance with the principles of the present disclosure.
Figure 19:
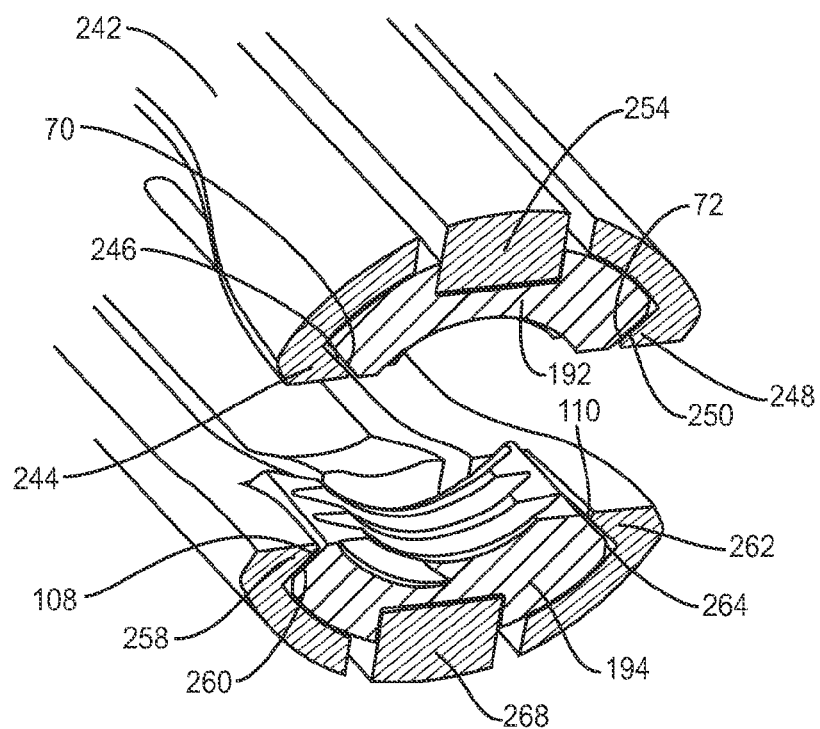
FIG. 19 is a break away perspective view of the components shown in FIG. 16.
Figure 20:
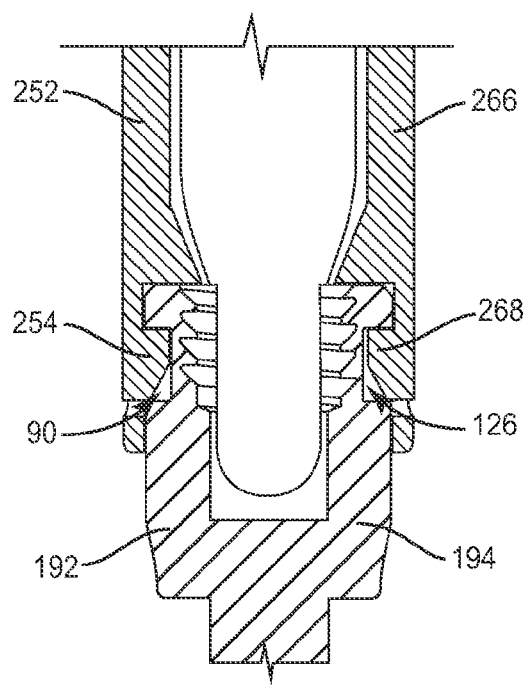
FIG. 20 is a break away side view in cross-section of the components shown in FIG. 16.

In use, as shown in FIG. 15, to treat the affected section of vertebrae V, a medical practitioner obtains access to a surgical site including vertebrae V1, V2 in any appropriate manner, such as through incision and retraction of tissues. It is envisioned that the spinal implant system may be used in any existing surgical method or technique including open surgery, mini-open surgery, minimally invasive surgery, and percutaneous surgical implantation, whereby vertebrae is accessed through a micro-incision, or sleeve that provides a protected passageway to the area. Once access to the surgical site is obtained, the particular surgical procedure is performed for treating the spinal disorder. The spinal implant system is then employed to augment the surgical treatment. The spinal implant system can be delivered or implanted as a pre-assembled device or can be assembled in situ. The components of the spinal implant system may be completely or partially revised, removed or replaced during or after the surgical procedure.

Pilot holes or the like are made in vertebrae V1, V2 for receiving shaft 198 of bone fastener 38. The spinal implant system is disposed adjacent vertebrae V at a surgical site and the components of spinal implant system are manipulable to drive, torque, insert or otherwise connect bone fastener 38 to vertebrae, according to the particular requirements of the surgical treatment.

Initially, extensions 32, 34 are disposed in the second orientation, described above, such that projections 92, 128 are not disposed in locking cavities 90, 126 (FIG. 13) and tips 178, 180 are disposed in lateral openings 52. Distal end 42 is distally into alignment with bone fastener 38 such that faces 64, 68 engage surfaces 70, 72 and faces 102, 106 engage surfaces 108, 110 to retain sleeve 30 with bone fastener 38 in a first orientation, as described above.

The U-shaped wall defined by ridge 49 and ledge 79 engages face 200 and the U-shaped wall defined by ridge 51 and ledge 115 engages face 202. Projections 92, 128 are aligned with locking cavities 90, 126 and chamfers 95, 135 slide along surfaces 91, 127 such that projections 92, 128 move into locking cavities 90, 126 to retain sleeve 30 with bone fastener 38.

Handle 162 is manipulated to cause axial translation of extensions 32, 34 relative to sleeve 30, to provisionally capture bone fastener 38. Buttons 182, 186 are engaged to permit actuator 36 to advance distally along longitudinal axis a. Distal ends 132, 148 engage ramps 84, 120 such that projections 92, 128 are not movable out of locking cavities 90, 126, as shown in FIG. 14. Projections 92, 128 are fixed within locking cavities 90, 126.

Sleeve 30 defines a cavity 204 configured for passage of instruments, such as, for example, a driver for applying torque and driving bone fastener 38 into vertebrae V1, V2 and/or a rod reduction instrument such that the instrument may be passed through cavity 204 and into implant cavity 46. Upon treatment employing the components of the spinal implant system, bone fastener 38 is ejected from sleeve 30 for fixation with vertebrae V1, V2.

To eject bone fastener 38 from sleeve 30, the medical practitioner engages buttons 182, 186 simultaneously. Actuator 36 is advanced proximally such that ends 132, 148 disengage ramps 84, 120, as described above, to allow projections 92, 128 to disengage from locking cavities 90, 126. Sleeve 30 is advanced proximally along longitudinal axis a, as described above, such that chamfers 95, 135 engage and slide along surfaces 91, 127. Projections 92, 128 are driven outwardly and out of engagement with locking cavities 90, 126, as shown in FIG. 13. Upon completion of the procedure, the surgical instruments and assemblies are removed from the surgical site and the incision is closed.

In one embodiment, tabs 74, 112 comprise a resilient configuration and/or material and are biased outwardly such that projections 92, 128 may pivot in and out of locking cavities 90, 126. Tabs 74, 112 are biased outwardly such that projections 92, 128 are spaced apart from locking cavities 90, 126 when sleeve 30 is engaged with bone fastener 38. To capture bone fastener 38 with sleeve 30, actuator 36 may be advanced distally such that portion 144 is advanced from end 86 to end 88 and portion 160 is advanced from end 122 to end 124 such that ends 132, 148 engage ramps 84, 120 to fix projections 92, 128 within locking cavities 90, 126 to capture bone fastener 38 with end 42. To remove sleeve 30 from bone fastener 38, actuator 36 may be advanced proximally such that portion 144 is advanced from end 88 to end 86 and portion 160 is advanced from end 124 to end 122 such that ends 132, 148 disengage ramps 84, 120 causing resilient tabs 74, 112 to pivot outwardly such that projections 92, 128 pivot out of engagement with locking cavities 90, 126 to release bone fastener 38 from distal end 42.

Bone fastener 38 may be employed as a bone screw, pedicle screw, or multi-axial screw used in spinal surgery. It is contemplated that bone fastener 38 may be coated with an osteoconductive material such as hydroxyapatite and/or osteoinductive agent such as a bone morphogenic protein for enhanced bony fixation. Bone fastener 38 can be made of radiolucent materials such as polymers. Radiomarkers may be included for identification under x-ray, fluoroscopy, CT, or other imaging techniques. Metallic or ceramic radiomarkers, such as tantalum beads, tantalum pins, titanium pins, titanium endcaps, and platinum wires can be used.

It is envisioned that the spinal implant system may include one or a plurality of extenders, inserters, rod reduction instruments, bone fasteners and/or vertebral constructs, which may be alternately sized and dimensioned, and arranged as a kit, according to the requirements of a particular application.

In one embodiment, shown in FIGS. 16-20, the spinal implant system, similar to the device and methods described above with regard to FIGS. 1-15, includes a sleeve 230 similar to sleeve 30, which defines a longitudinal axis a1 and extends between a proximal end 232 and a distal end 234. Sleeve 230 includes a concavely curved inner surface 236 defining an implant cavity 238 and a convexly curved outer surface 240.

Sleeve 230 includes a first arm 242 including a first flange 244 having a planar face 244 extending perpendicular to longitudinal axis a1 and a second flange 248 having a planar face 250 extending perpendicular to longitudinal axis a1 adjacent distal end 234 of sleeve 230. Planar faces 246, 250 are configured to engage axial end surfaces 70, 72 to engage sleeve 230 with first wall 192 and prevent sleeve 230 from rotating relative to bone fastener 38 about longitudinal axis a1. First arm 242 includes a movable tab 252, which includes an inward projection 254 extending transverse to longitudinal axis a1 from inner surface 236 and configured for fixation with locking cavity 90 to capture bone fastener 38 with distal end 234 of sleeve 230.

Sleeve 230 includes a second arm 256 including a first flange 258 having a planar face 260 extending perpendicular to longitudinal axis a1 and a second flange 262 having a planar face 264 extending perpendicular to longitudinal axis a1 adjacent distal end 234 of sleeve 230. Planar faces 260, 262 are configured to engage axial end surfaces 108, 110 to engage sleeve 230 with second wall 194 and prevent sleeve 230 from rotating relative to bone fastener 38 about longitudinal axis a1. Arm 256 includes a movable tab 266, which includes an inward projection 268 extending transverse to longitudinal axis a1 from inner surface 236 and configured for fixation with locking cavity 126 to capture bone fastener 38 with distal end 234 of sleeve 230.

To provisionally capture bone fastener 38, sleeve 230 is positioned relative to bone fastener 38 such that projections 254, 268 are longitudinally aligned with locking cavities 90, 126. Sleeve 230 is advanced distally along longitudinal axis a2 until projections 254, 268 engage locking cavities 90, 126 causing projections 254, 268 to be disposed in locking cavities 90, 126 to capture bone fastener 38 with distal end 234.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A sleeve extending along a longitudinal axis between a first end and a second end, the sleeve including a first arm, a second arm and an inner surface defining an interior cavity therebetween, the first end comprising a smooth outer surface, the smooth outer surface extending from a proximal end surface of the first end to the arms, each of the arms including a radially flexible tab having an inward projection, wherein each of the tabs is resiliently biased in a direction that faces the other tab such that the sleeve is movable between a first orientation in which the projections are spaced apart a first distance and a second orientation in which an outward force is exerted on each tab such that the projections are spaced apart from one another a second distance that is greater than the first distance, wherein each tab has a convex end surface extending between planar sidewalls and a uniform width between the sidewalls and the convex end surface has a maximum width that is equal to the width of the tab.

2. The sleeve of claim 1, wherein:
the first end includes a first end surface;
the second end includes a second end surface; and
the arms include a gap extending through inner and outer surfaces of each arm without extending through the first end surface of the sleeve or the second end surface of the sleeve, the gaps defining the tabs.

3. The sleeve of claim 1, wherein the convex end surface defines a perimeter of the projection.

4. The sleeve of claim 1, wherein the sleeve is free of any gaps extending through the inner surface that extend through axes defined by the tabs.

5. The sleeve of claim 1, wherein the tabs each include a tapered portion positioned proximal of the projection, the tapered portion having a maximum thickness that is greater than a maximum thickness of the projection.

6. The sleeve of claim 1, wherein:
a transverse axis extends perpendicular to the longitudinal axis;
the first and second arms each include a first flange and a second flange;
the first flange is disposed at an acute angle relative to the transverse axis; and
the second flange is disposed at an angle relative to the transverse axis that is inverse of the acute angle.

7. The sleeve of claim 6, wherein the first and second flanges each include a planar surface configured to engage opposite planar end surfaces of a wall of a bone fastener that defines an implant cavity to fix the sleeve with the bone fastener.

8. A spinal implant system comprising:
a sleeve extending along a longitudinal axis between a first end and a second end, the sleeve including a first arm, a second arm and an inner surface defining an interior cavity therebetween, each of the arms including a movable tab having an inward projection the first end comprising a smooth outer surface, the smooth outer surface extending from a proximal end surface of the first end to the arms; and
a bone fastener comprising a proximal portion including two spaced apart walls defining an implant cavity extending perpendicular to the longitudinal axis and a distal portion including a tissue penetrating portion, the walls each including first and second end surfaces extending parallel to the longitudinal axis and an outer surface extending between the first and second end surfaces, the outer surfaces of the walls each defining a locking cavity,
wherein the first and second end surfaces are each disposed at an acute angle relative to the implant cavity and the first and second arms each include a first flange and a second flange and the first flange engages the first end surface of a respective wall and the second flange engages the second end surface of the respective wall when the sleeve is in both the first and second orientations the to prevent disengagement of the arms from the bone fastener
wherein the sleeve is movable between a first orientation such that the projections are spaced apart from the locking cavities and a second orientation such that the projections are disposed in a respective locking cavity to fix the sleeve with the bone fastener.

9. The spinal implant system of claim 8, wherein the first and second end surfaces are planar and the first and second flanges each include a planar surface that engages a respective end surface.

10. The spinal implant system of claim 8, wherein the outer surfaces of the walls each include a tapered edge surface that defines one of the locking cavities, the projections each including a chamfer surface engageable with one of the edge surfaces such that the sleeve is axially translatable to force the projections out of engagement with the locking cavities to move the sleeve from the second orientation to the first orientation.

11. The spinal implant system of claim 8, wherein:
the first end includes a first end surface;
the second end includes a second end surface; and
the arms include a gap extending through inner and outer surfaces of each arm without extending through the first end surface of the sleeve or the second end surfaces of the sleeve, the gap defining the tab.

12. The spinal implant system of claim 8, wherein the tab has a convex end surface extending between planar sidewalls, the convex end surface defining a perimeter of the projection.

13. The spinal implant system of claim 8, wherein:
the tab has a convex end surface extending between planar sidewalls;
the first and second arms each have a length extending between a proximal end and the second end of the sleeve, a length of the interior cavity being defined by the lengths of the first and second arms.

14. The spinal implant system of claim 8, wherein:
the tabs each include a ledge extending perpendicular to the longitudinal axis positioned proximal of the projection;
the projections each include proximal and distal surfaces extending perpendicular to the longitudinal axis;
the implant cavities each include proximal and distal surfaces extending perpendicular to the longitudinal axis;
the walls each include a proximal end surface extending perpendicular to the longitudinal axis; and
the ledge engages the proximal end surfaces of the walls, the proximal surfaces of the projections engage the proximal surfaces of the implant cavities and the distal surfaces of the projections engage the distal surface of the implant cavities when the sleeve is in the second orientation.

15. The spinal implant system of claim 14, wherein the ledge has a maximum thickness that is greater than a maximum thickness of the projection.

16. A spinal implant system comprising:
a sleeve extending along a longitudinal axis between a first end surface of a first end and a second end surface of a second end, the sleeve including a first arm, a second arm and an inner surface defining an interior cavity therebetween, each of the arms including a first flange, a second flange and a gap extending through inner and outer surfaces without extending through the first and second end surfaces, the gap defining a radially flexible, resiliently biased tab having a convex end surface extending between planar sidewalls, the tab having an inward projection including a chamfer surface, the first and second arms each having a length extending between a proximal end and the second end surface of the sleeve, a length of the interior cavity being defined by the lengths of the first and second arms, the tabs each including a tapered portion positioned proximal of the projection, the tapered portion having a maximum thickness that is greater than a maximum thickness of the projection; and a bone fastener comprising a proximal portion including two spaced apart walls defining an implant cavity extending perpendicular to the longitudinal axis and a distal portion including a tissue penetrating portion, the walls each including a first end surface, a second end surface and an outer surface extending therebetween, the outer surface defining a locking cavity having a beveled edge, wherein the first and second end surfaces of the bone fastener are planar and are disposed at an acute angle relative to the implant cavity, the first end surface of the bone fastener being disposed at angle that is inverse to an angle at which the second end surface of the bone fastener is disposed, the first and second flanges each including a planar surfaces that engages a respective end surface of the bone fastener, wherein the sleeve is movable between a first orientation such that the projections are spaced apart from the locking cavities and a second orientation such that the each of the projections is disposed in a respective locking cavity to fix the sleeve with the bone fastener, wherein the sleeve is axially translatable such that the chamfer surfaces slide along the beveled edges to force the projections out of engagement with the locking cavities to move the sleeve from the second orientation to the first orientation, and wherein the flanges engage the first and second end surfaces of a respective wall when the sleeve is in both the first and second orientations to prevent disengagement of the arms from the bone fastener.

* * * * *